(12) United States Patent
Pesu et al.

(10) Patent No.: US 8,716,632 B1
(45) Date of Patent: May 6, 2014

(54) CERAMIC SCENT BOWL AND METHOD FOR HEATING A SCENT BOWL

(75) Inventors: Maxine Pesu, Gilbert, AZ (US); Fatima Silva, Queen Creek, AZ (US); Stephanie Tierney, Coolidge, AZ (US); Leann Waisath, Chandler, AZ (US); Lynae Parrott, Gilbert, AZ (US)

(73) Assignee: Gold Canyon International, LLC, Chandler, AZ (US)

( * ) Notice: Subject to any disclaimer, the term of this patent is extended or adjusted under 35 U.S.C. 154(b) by 0 days.

(21) Appl. No.: 13/204,545

(22) Filed: Aug. 5, 2011

Related U.S. Application Data

(63) Continuation-in-part of application No. 12/107,962, filed on Apr. 23, 2008.

(60) Provisional application No. 61/371,164, filed on Aug. 5, 2010.

(51) Int. Cl.
*F27D 11/00* (2006.01)
*F24F 6/00* (2006.01)

(52) U.S. Cl.
USPC ........... 219/438; 219/433; 392/390; 392/391; 392/392; 392/393; 392/394; 392/395; 392/386; 392/438; 392/429; 392/423

(58) Field of Classification Search
USPC ........... 219/438, 433; 392/390–95, 386, 438, 392/429, 432–3
See application file for complete search history.

(56) References Cited

U.S. PATENT DOCUMENTS

| | | |
|---|---|---|
| 5,651,942 A | 7/1997 | Christensen |
| 6,106,786 A | 8/2000 | Akahoshi |
| 6,234,786 B1 | 5/2001 | Wagner |
| 6,354,710 B1 | 3/2002 | Nacouzi |
| 6,361,752 B1 | 3/2002 | Demarest et al. |
| 6,413,476 B1 | 7/2002 | Barnhart |
| 6,627,857 B1 | 9/2003 | Tanner et al. |
| 6,733,548 B2 | 5/2004 | Rasmussen et al. |
| 7,028,917 B2 | 4/2006 | Buthier |
| 7,046,919 B2 * | 5/2006 | Shimizu et al. ............... 392/390 |
| D522,671 S | 6/2006 | Niemeyer |
| 7,067,772 B2 | 6/2006 | Tanner et al. |
| 7,132,084 B1 | 11/2006 | Roumpos |
| 7,133,605 B2 | 11/2006 | Niemeyer |
| 7,195,739 B1 | 3/2007 | Penman et al. |
| D542,437 S | 5/2007 | Snow |
| 7,329,839 B2 | 2/2008 | Palmer |
| 2002/0152672 A1 | 10/2002 | Rasmussen et al. |
| 2003/0007887 A1 | 1/2003 | Roumpos et al. |
| 2004/0250464 A1 | 12/2004 | Rasmussen et al. |

(Continued)

*Primary Examiner* — Shawntina Fuqua
(74) *Attorney, Agent, or Firm* — Booth Udall Fuller, PLC

(57) ABSTRACT

A scent bowl may include a base having an external concave base surface and at least one sidewall extending from the base. A majority of the base and the at least one sidewall may be formed of ceramic material. A system for scenting the air in a room with scent from a scent bowl may include a scent bowl warmer configured to generate heat at a first temperature and a detachable and separate scent bowl including a base having an external concave base surface and at least one sidewall extending from the base and a scent emitter therein, the scent emitter having a fragrance and a second temperature at which the fragrance evaporates. The first temperature is high enough to evaporate at least a portion of the fragrance from the scent emitter in the bowl in less than three hours.

19 Claims, 8 Drawing Sheets

(56) References Cited

U.S. PATENT DOCUMENTS

| | | |
|---|---|---|
| 2005/0016985 A1 | 1/2005 | Haas et al. |
| 2005/0150886 A1 | 7/2005 | Niemeyer |
| 2005/0163649 A1 | 7/2005 | Friedrich et al. |
| 2006/0006582 A1 | 1/2006 | Strelnieks |
| 2006/0018786 A1 | 1/2006 | Tolman et al. |
| 2006/0239870 A1 | 10/2006 | Schutte et al. |
| 2006/0240371 A1 | 10/2006 | Palmer |
| 2007/0047931 A1 | 3/2007 | Niemeyer |

* cited by examiner

CERAMIC SCENT BOWL AND METHOD FOR HEATING A SCENT BOWL

CROSS REFERENCE TO RELATED APPLICATIONS

This application is a continuation-in-part application of the earlier U.S. Utility patent application entitled "PLASTIC SCENT POD AND METHOD FOR HEATING A SCENT POD," application Ser. No. 12/107,962, filed Apr. 23, 2008, now pending, and claims the benefit of the filing date of U.S. Provisional Patent Application Ser. No. 61/371,164 entitled "CERAMIC SCENT BOWL AND METHOD FOR HEATING A SCENT BOW" filed on Aug. 5, 2010, the disclosures of all of which being hereby incorporated entirely herein by reference.

BACKGROUND

1. Technical Field

Aspects of this document relate to heated scent-emitting products.

2. Background Art

Conventional scent-emitting devices exist. Such devices have been used to add fragrance to rooms. Fragrance may be added to a room for purely aesthetic reasons, for purposes of aroma therapy, or to mask undesirable odors such as cooking odors, smoke, mildew and the like. Conventional scent-emitting devices may comprise a fragrance carried in a substrate such as wood, paper, cloth, gel, plastic, ceramic, liquid, or other compound or material suitable for fragrance carrying. Conventional scent-emitting devices rely on air movement, heat, or other energy input in order to effectively disperse a fragrance. Conventional "fragrances" may comprise a simple perfume, an essential oil, or other aroma compound.

Some examples of conventional scent-emitting products more closely related to the present disclosure include scented candles, scented wickless candles (on a warming plate), scented wax chips, and the like. Scented candles and scented wickless candles conventionally are held in holders (to withstand the flame or heat applied to or by the product) or, in the case of some candles, are left free-standing without a container. One particular implementation of a scented wickless candle known in the prior art includes a warmer and scented wax contained in a metal container that includes a metal base and metal sides, with a hard plastic rim glued to the top of the metal sides with a hard plastic lid removably coupled to the hard plastic rim.

SUMMARY

Aspects of this document relate to heated scent-emitting products. These aspects may comprise, and implementations may include, one or more or all of the components and steps set forth in the appended CLAIMS, which are hereby incorporated by reference.

In one aspect, a scent bowl may include a base having an external concave base surface and at least one sidewall extending from the base. The base of the bowl may also have an internal flat base surface. The majority of the base and the at least one sidewall is formed of a ceramic material or any inorganic clay material such as porcelain or even alloys and metals that can maintain a similar temperature profile to ceramic material.

Particular implementations may include one or more of the following.

The at least one sidewall may taper outwardly. The bowl may be detachable and separate from any scent warmer device. Scented oil may be provided for use with the bowl. Alternatively, scented wax may be provided inside the bowl, the scented wax comprising a fragrance and a first temperature at which the scented wax liquefies and evaporates fragrance. The external concave base surface may define a pocket where heated air generated from the scent bowl warmer is trapped. Such trapped, heated air may aid in the constant temperature achieved by the ceramic bowl when in use on the scent warmer. An upper edge of the at least one sidewall may include a lip that forms a top edge of the bowl and is configured to allow a user to pick up the bowl, especially when on the scent bowl warmer. The bowl may have a thickness of at least 1.5 to 2.5 millimeters, such as about 2 millimeters for example.

In another aspect, a system for scenting the air in a room with scent from a scent bowl may include a scent bowl warmer configured to generate heat at a first temperature and a detachable and separate scent bowl including a base having an external concave base surface and at least one sidewall extending from the base and a scent emitter therein, the scent emitter having a fragrance and a second temperature at which the fragrance evaporates. The first temperature is high enough to evaporate at least a portion of the fragrance from the scent emitter in the bowl in less than three hours.

Particular implementations may include one or more of the following.

The majority of the base and the at least one sidewall is formed of a ceramic material or any inorganic clay material such as porcelain or even alloys and metals that can maintain a similar temperature profile to ceramic material). The at least one sidewall may taper outwardly. The bowl may be detachable and separate from any scent warmer device. Scented oil may be provided for use with the bowl. Alternatively, scented wax may be provided inside the bowl, the scented wax comprising a fragrance and a first temperature at which the scented wax liquefies and evaporates fragrance. The base of the bowl may also have an internal flat base surface. The external concave base surface may define a pocket where heated air generated from the scent bowl warmer is trapped. Such trapped, heated air may aid in the constant temperature achieved by the ceramic bowl when in use on the scent warmer. An upper edge of the at least one sidewall may include a lip that forms a top edge of the bowl and is configured to allow a user to pick up the bowl, especially when on the scent bowl warmer. The bowl may have a thickness of at least 1.5 to 2.5 millimeters, such as about 2 millimeters for example. The first temperature may be set so that it is no greater than 230° Fahrenheit. The second temperature may be approximately 175° Fahrenheit. The scent emitter may be one of scented oil and scented wax.

In still another aspect, a method for scenting the air in a room from a ceramic scent bowl is provided. The method includes placing an external concave base surface of a detachable and separate ceramic scent bowl on a scent bowl warmer surface. The ceramic scent bowl includes one of a fragrance oil and a scented wax and fragrance within the bowl. Then heating the external concave base surface through the ceramic scent bowl warmer surface by heating the ceramic scent bowl warmer surface to a temperature sufficient to completely liquefy the wax and evaporate at least a portion of the fragrance from the wax or oil in less than three hours.

The foregoing and other aspects, features, and advantages will be apparent to those of ordinary skill in the art from the DESCRIPTION and DRAWINGS, and from the CLAIMS.

BRIEF DESCRIPTION OF THE DRAWINGS

Implementations will hereinafter be described in conjunction with the appended DRAWINGS (which are not necessarily to scale), where like designations denote like elements, and.

DESCRIPTION

In the following description, reference is made to the accompanying DRAWINGS which form a part hereof, and which show by way of illustration possible implementations. It is to be understood that other implementations may be utilized, and structural, as well as procedural, changes may be made without departing from the scope of this document. As a matter of convenience, various components will be described using exemplary materials, sizes, shapes, dimensions, and the like. However, this document is not limited to the stated examples and other configurations are possible and within the teachings of the present disclosure.

Plastic Scent Pod

It has been determined that for most social gatherings where a scent pod and scent pod warmer surface is used, it is most desirable if fragrance begins to evaporate within 3 hours, and more desirable that it evaporate within 2 hours. In particular implementations, it is desirable for fragrance to evaporate in less than 1 hour. For specific implementations where the scent emitter is scented wax, it is desirable if the fragrance evaporates from the liquefied wax within 3 hours, or more preferably in less than 2 hours. In particular implementations, it is desirable for the scented wax to completely liquefy and fragrance to evaporate in less than 1 hour.

It is believed that, different from the conventional containers, a plastic container will be more desirable from a safety and marketing standpoint and that it will provide production advantages as well. However the use of plastic as a container on a heating element, and particularly on a heating element when the plastic container contains melted wax presents its own safety and use concerns. One challenge in using a plastic container is that plastic itself can melt from the heating element, causing the sides of the plastic container to deform and present safety hazards. The use of wax inside the plastic container compounds the heating problems. To use a plastic container, a balance needs to be had between the temperature of the scent pod warmer surface, the melting point of the scented wax (if used), the thickness of the wax (if used), and the plastic used to form the plastic container. If the temperature is too high or the plastic heat deflection temperature of the plastic too low, the plastic may melt when exposed too long to the warmer surface. Additionally, if the wax has too high a melting point or is too thick, the wax may not liquefy completely from the heat of the warmer plate resulting in an ineffective fragrance disbursement.

Figure 1:
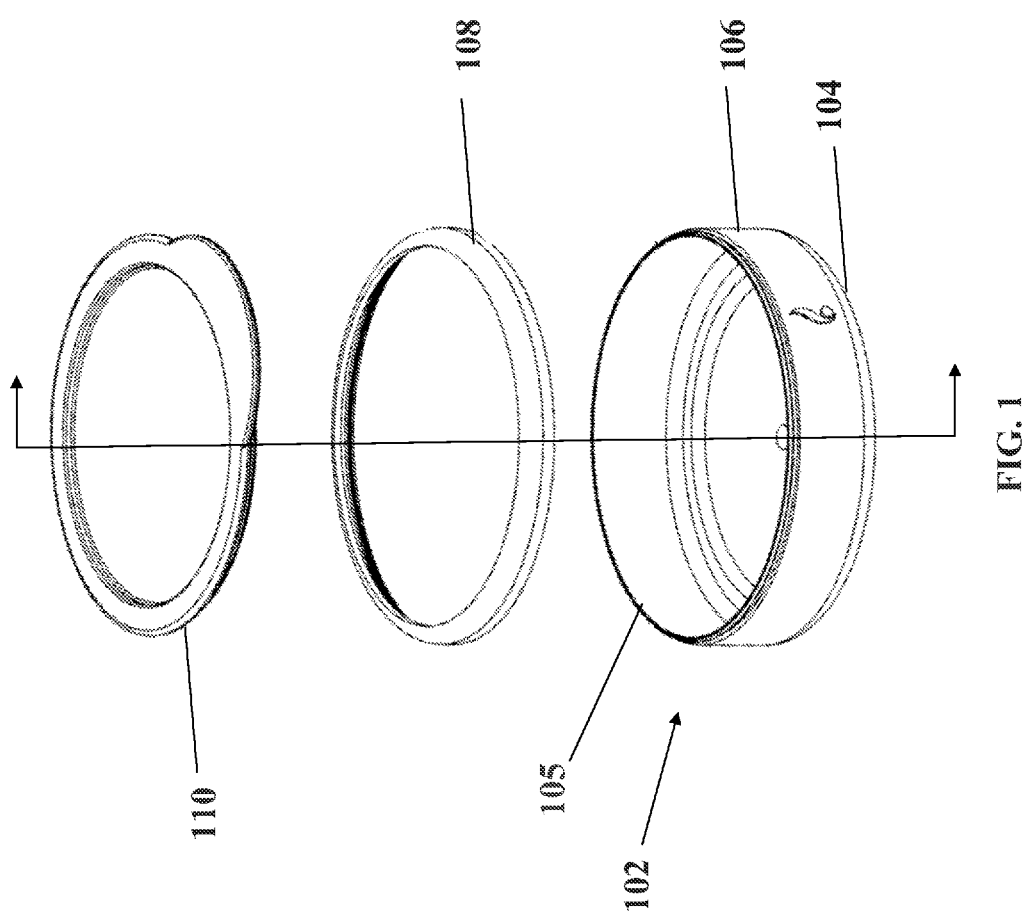
FIG. 1 is an exploded view of a scent pod container.
Figure 2:
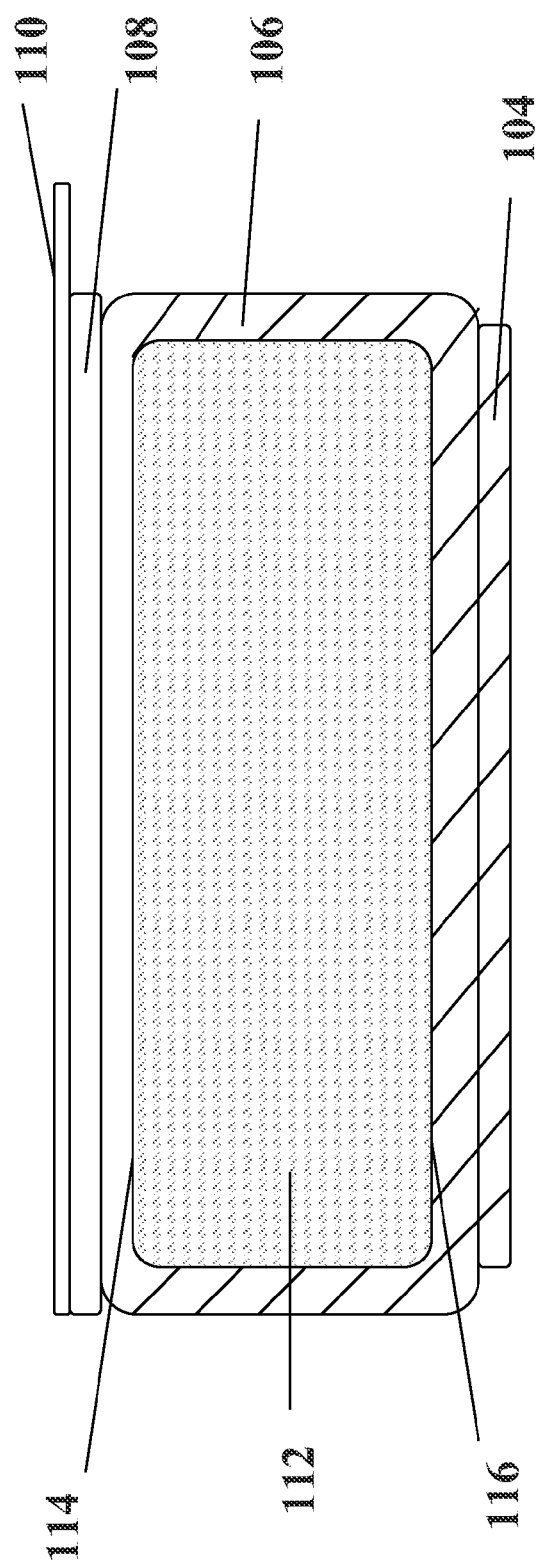
FIG. 2 is a cross sectional view of a scent pod container.

With reference to FIGS. 1-2, a break apart view and a cross-sectional view of a scent pod container are illustrated, respectively. Scent pod 100 may comprise base 104, brim 105, and side wall 106, lip ring 108, and removable lid 110. Scent pod container 102 may comprise base 104, brim 105, and side wall 106. The components defining scent pod 100 may be formed integrally or formed separately and then joined together. For this particular implementation, scent pod container 100 (and one or more components thereof) may be formed with a majority of the container 100 made of plastic having a thickness of at least 0.1 millimeters (mm). In other particular implementations, portions of the scent pod container 100 may be formed to include some other materials, such as, by non-limiting example, a metal base or metal portions of the sides. In some implementations, lip ring 108 may be removably coupled with brim 105. Removable lid 106 may be removably coupled with scent pod container 102 via lip ring 108, or directly with the brim 105 of the base 104 in implementations where no lip ring 108 is used. Base 104 may comprise a flat base surface. In other particular implementations, a curved base surface may be used, but it is desirable to have the shape of the scent pod base surface mate with the surface of the scent pod warmer surface to enable more efficient heat transfer. It is not required, however, that they mate exactly.

In one particular implementation shown in FIG. 1, the material comprising the flat base surface has a thickness of at least 1.0 millimeters (mm) and is formed of a translucent or a transparent plastic. The plastic forming scent pod 100 (and/or its components) may comprise a heat deflection temperature measured using ASTM standard D648 at a pressure of 66 psi of at least 257° Fahrenheit without deformation for unannealed plastic. It will be understood that "heat deflection temperature" refers to the temperature at which a plastic deforms. For safety, scent pods are required to withstand temperatures much higher than a typical warmer surface will generate, and for a much longer time. Accordingly, research was conducted and numerous plastics were tested in determining which plastics could withstand the rigorous testing processes while the scented wax liquefied and yet provide translucent or transparent view of the scented wax within the container. There are very few plastics which are transparent or translucent and which also have a heat deflection temperature of at least 257° Fahrenheit. Samsung Total HJ730 plastic by Samsung Total Petrochemicals Co., Ltd. Is one found to work for the specific examples provided in this disclosure. This plastic also comprises a Underwriters' Laboratories Relative Temperature Index Strength (UL RTI) measured using UL 746 of at least 115° Centigrade. It will be understood that UL RTI refers to a material's thermal endurance. In particular, UL RTI is used to determine the effective life of a plastic article, determined by accelerated aging or deterioration of the plastic at elevated temperatures.

Still referring to FIGS. 1-2, scent pod container 102 may contain a scent emitter 112 in the form of scented wax 112, which comprises a scented wax bottom surface 116 in surface communication with base 104, and scented wax upper surface 114. Scented wax 112 may comprise any animal wax, vegetable wax, mineral wax, petroleum wax or synthetic wax in compound with a fragrance. A fragrance may comprise any perfume, essential oil, or other aromatic compound, whether derived from a plant source, animal source, other natural source, or any synthetic source. It will be understood that where liquid fragrance is compounded with wax, the liquid fragrance may remain in its liquid state and may reside in the interstitial spaces between individual wax crystals. In one particular implementation shown in FIG. 1, the scented wax 112 is formed of the same wax scented candles are made of One example of a company that manufactures and sells scented candles is Gold Canyon International, Inc. of Arizona, USA. Wax, depending upon its physical properties related to the type of wax used, has a temperature at which it melts. Scented wax is wax that includes fragrance mixed with the wax. When the wax melts from a solid to a liquid, the fragrance trapped in the previously solid wax now turned liquid begins to evaporate. In a particular implementation of scented wax 112, the temperature at which scented wax 112 liquefies and evaporates fragrance is between 140° and 170° Fahrenheit. In other implementations, the temperature at which scented wax 112 liquefies and evaporates fragrance is above about 113° Fahrenheit.

Figure 5:
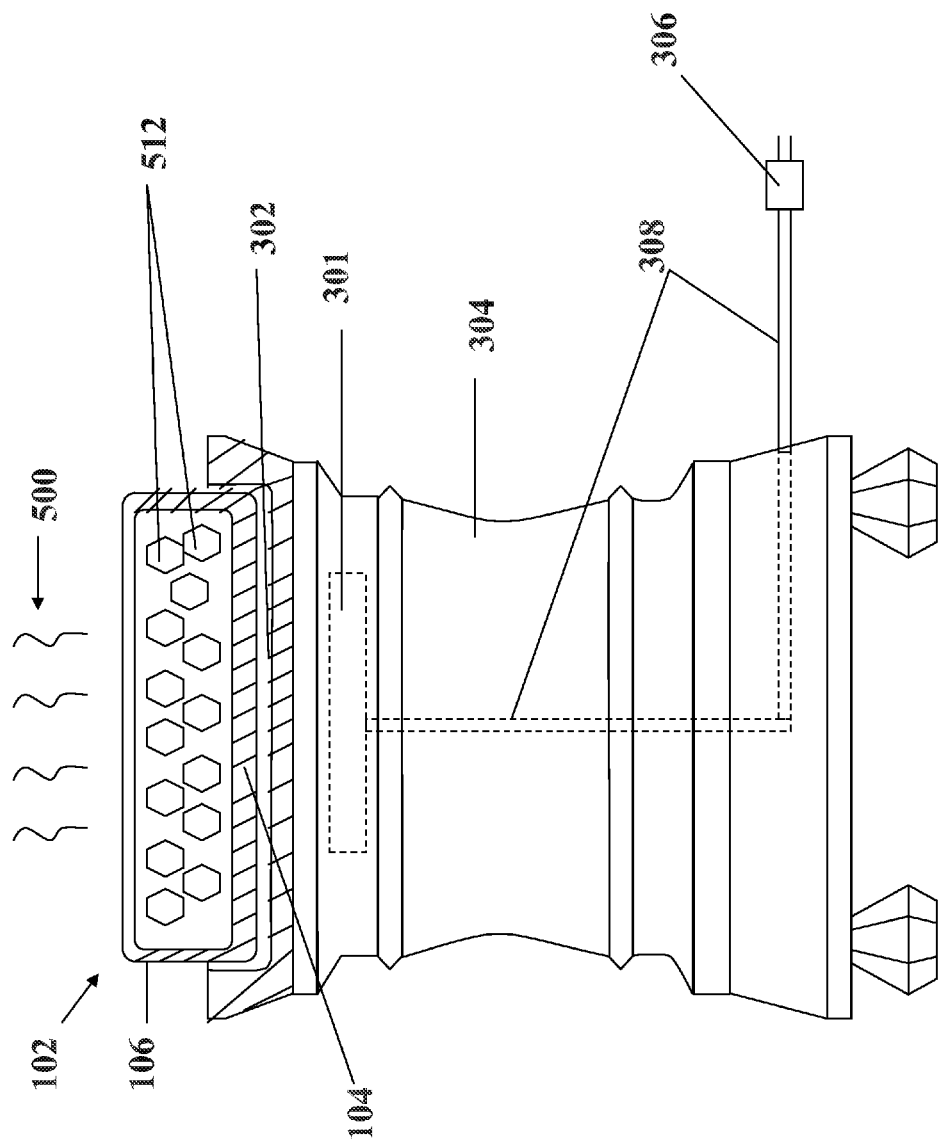
FIG. 5 is an in-use view of a scent pod containing a second form of a scent emitter placed on a scent pod warmer.

In particular implementations, and as shown in the in-use view provided in FIG. 5, scent pod container 102 may contain a scent emitter in other forms. Other forms of scent emitters include any substrate capable of carrying a fragrance such as, without limitation, wood, paper, cloth, felt, gel, plastic, ceramic, glass, liquid, or other compound or material suitable for carrying a fragrance. It will be understood that, in implementations involving a scent emitter, the scent emitter may first be formed and thereafter impregnated with a fragrance, or the substrate may be impregnated with fragrance simultaneously with its forming.

Figure 3:
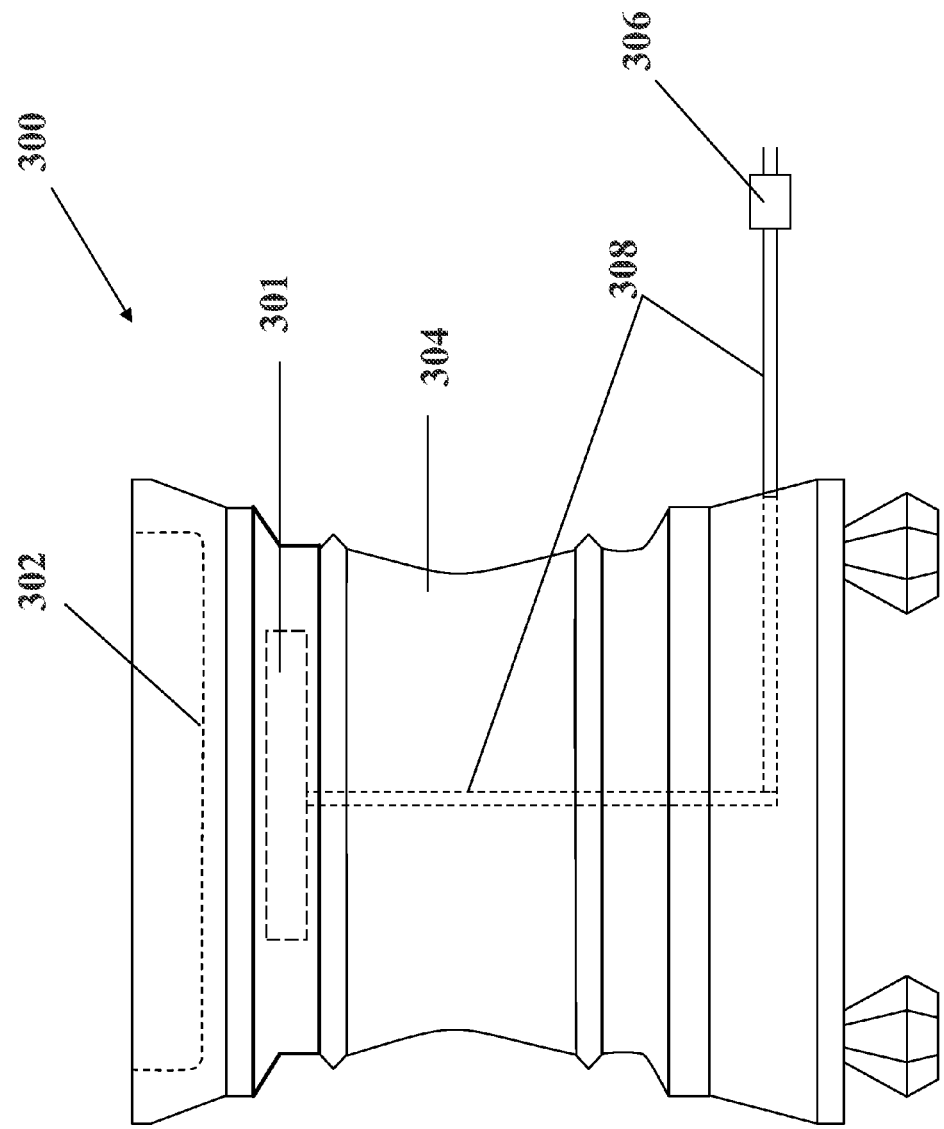
FIG. 3 is a perspective view of a scent pod warmer.

FIG. 3 illustrates a perspective view of a scent pod warmer. Scent pod warmer 300 may comprises scent pod warmer surface 302 and warmer base 304. The scent pod warmer surface 302 is heated with electricity or a flame in limited implementations, or other heating element. In the particular implementation illustrated in FIG. 3, the scent pod warmer surface 302 comprises electric resistor 301, which may be in electrical communication with a power outlet via power plug 306 and electrical cord 308. Other heating elements are known in the art and are equally interchangeable with the non-limiting example provided here. Those of ordinary skill in the art can readily select appropriate materials for creating a warmer surface with a desired temperature. With power plug 306 inserted in a power outlet, electricity flows through electrical cord 308 to electrical resistor 301. Electrical resistor 301 converts the electrical energy into heat energy. In particular implementations, scent pod warmer surface 302 itself may comprise electrical resistor 301 or other resistive or other heating element. In other implementations, electrical resistor 301 may be coupled with scent pod warmer surface 302 or adjacent to or separated from scent pod warmer surface 302. In particular implementations, for safety, the temperature of scent pod warmer surface 302 is designed so that it does not exceed 230° Fahrenheit.

Figure 4:
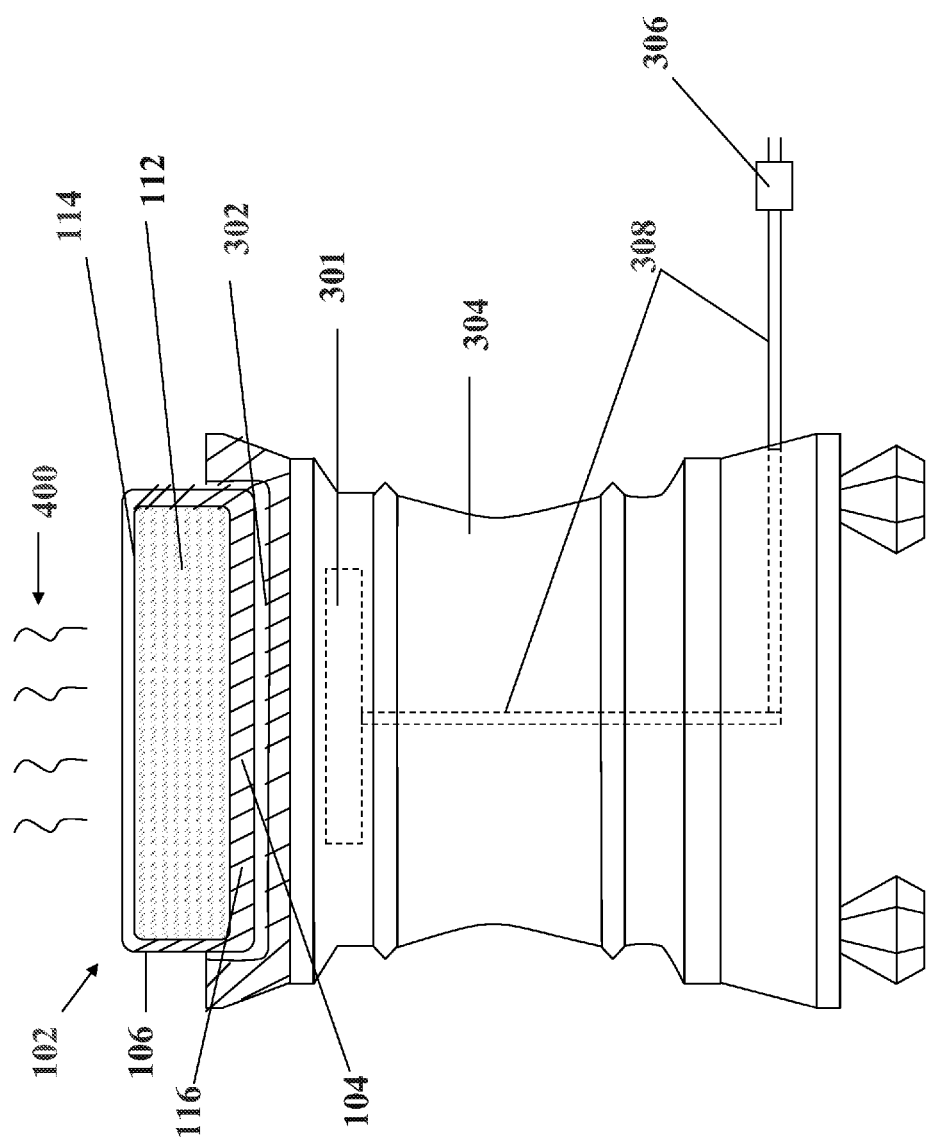
FIG. 4 is an in-use view of a scent pod containing a scent emitter in the form of a scented wax, the scent pod placed on a scent pod warmer.

Referring to FIG. 4, an in-use view of a scent pod containing scented wax and placed on a scent pod warmer is illustrated. A user may place scent pod container 102 on scent pod warmer 300 so that base 104 of scent pod container 102 is in thermal communication with scent pod warmer surface 302 of scent pod warmer 300. When the temperature of scent pod warmer surface 302 begins to increase (with base 104 of scent pod container 102 placed thereupon), the plastic comprising base 104 also begins to increase in temperature. Additionally, the thermal energy conducted from scent pod warmer surface 302 through base 104 continues to be conducted to scented wax bottom surface 116, through scented wax 112, until it escapes through scented wax upper surface 114 (which may carry fragrance 400 with it). When heated from the bottom through the plastic comprising the base 104, the scented wax 112 liquefies beginning with the scented wax bottom surface 116, slowly through the scented wax 112 until the scented wax upper surface 114 liquefies. Generally, the scented wax upper surface 114 begins liquefying at the center and moves outward to the edges until all of the scented wax upper surface 114, and all of the scented wax 112 below it, is completely liquefied.

The surface area of the liquefied scented wax upper surface 114 determines the amount of fragrance that evaporates from the scented wax 112. The greatest fragrance evaporation efficiency occurs when scented wax upper surface 114 has completely liquefied. For the scented wax 112 used in the particular implementation described above, the scented wax liquefies most efficiently, and safely, at a temperature range of between 140° and 170° Fahrenheit. It was found through testing that with approximately ¾ inches thick of scented wax in a plastic container having a base thickness of around 1.8 millimeters and an opening diameter of about 3¼ inches, the scented wax could be completely liquefied in the plastic container in less than 3 hours without deforming the plastic container and with the plastic container passing its standard safety tests. Temperatures closer to the bottom of the range yielded a longer melting time than temperatures closer to the top of the range. In other implementations, scented wax 112 takes less than two hours to completely liquefy. In still other implementations, scented wax 112 takes less than one hour to completely liquefy. It will be understood that the time in which scented wax 112 completely liquefies may vary depending upon the temperature of scent pod warmer surface 302, the thickness of base 104 of scent pod container 102, the thickness of scented wax 112 within scent pod container 102, the melting point of scented wax 112, the ambient room temperature, and other factors.

Still referring to FIG. 4, scent pod warmer surface 302 may be required to generate sufficient heat to completely liquefy scented wax 112 in less than three hours without deforming the plastic comprising scent pod 100. Accordingly, in particular implementations, the plastic forming scent pod 100 has a sufficient heat deflection temperature to withstand the heat generated by scent pod warmer surface 302 without deforming. Although the heat deflection temperature of the plastic used in the example with reference to FIG. 1 is 257° Fahrenheit, plastics with other heat deflection temperatures are also possible and contemplated. The number of possibilities of different heat deflection temperatures, wax melting points, warmer surface temperatures, plastic thicknesses and ambient temperatures is too great to provide all examples and it is believed that one of ordinary skill in the relevant art can readily design other plastic scent pod containers for use with scent pod warmers that heat to efficiently disperse fragrance from a scent emitter in a desirable time without deforming the plastic.

FIG. 5 illustrates an in-use view of a scent pod containing another example of a scent emitter placed on a scent pod warmer. Just as with the non-limiting example provided in FIG. 4, a user may place scent pod container 100 on scent pod warmer 300 so that base 104 of scent pod container 102 is in thermal communication with scent pod warmer surface 302 of scent pod warmer 300. When the temperature of scent pod warmer surface 302 begins to increase (with base 104 of scent pod container 102 placed thereupon), the plastic comprising base 104 begins to increase in temperature. Additionally, the thermal energy conducted from scent pod warmer surface 302 through base 104 is conducted to scent emitter 512 (which may comprise a substrate and a fragrance 500). In particular implementations, the substrate is a plastic bead infused with fragrance during production. As the plastic bead heats, it softens and a portion of the fragrance is permitted to evaporate from the plastic bead. In other particular implementations, a gel bead may be used.

As the scent emitter 512 increases in temperature, at least a portion of the fragrance 500 evaporates. In some implementations, with scent pod warmer surface 302 at a temperature of about 150° to 170° Fahrenheit, a portion of the fragrance may take less than three hours to evaporate. In other implementations, a portion of the fragrance may take less than two hours to evaporate. In still other implementations, a portion of the fragrance may take less than one hour to evaporate. It will be understood that the time in which a portion of the fragrance evaporates may vary depending upon the temperature of scent pod warmer surface 302, the thickness of base 104 of scent pod container 102, the amount of scent emitter within scent pod container 102, the ambient room temperature, and other factors. Selection of a suitable plastic for the container may be made using the principles discussed with reference to the example of FIG. 4.

Still referring to FIG. 5, scent pod warmer surface 302 is configured to generate sufficient heat to evaporate a portion of fragrance comprising scent emitter 512 in less than three hours without deforming the plastic comprising scent pod 100. Accordingly, in implementations, the plastic forming scent pod 100 may have a sufficient heat deflection temperature to withstand the heat generated by scent pod warmer surface 302 without deforming. Heating a plastic container, and particularly a transparent or translucent plastic container without the hot wax inside applies less stress to the sides of the plastic container because the hot liquid is not pressing out on the sides, but still requires careful selection of a suitable plastic and heating temperature ranges.

In places where the description above refers to particular implementations of a scent pod, it should be readily apparent that a number of modifications may be made without departing from the spirit thereof and that these implementations may be applied to other scent pods.

Scent Bowl

This document features scent bowl and method implementations. There are many features of scent bowl and method implementations disclosed herein, of which one, a plurality, or all features or steps may be used in any particular implementation. The foregoing and other aspects, features, and advantages will be apparent to those of ordinary skill in the art from this DESCRIPTION and the DRAWINGS.

Figure 6:
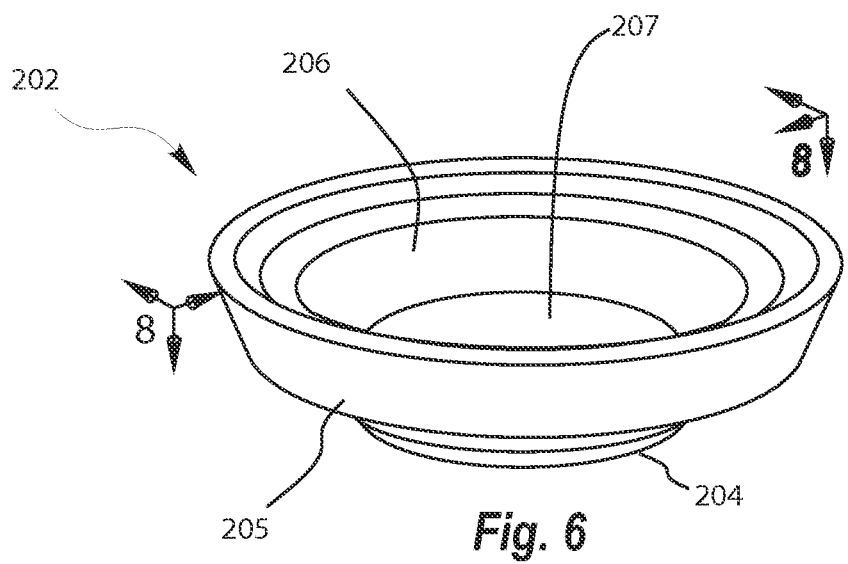
FIG. 6 is a perspective view of a ceramic scent bowl.
Figure 7:
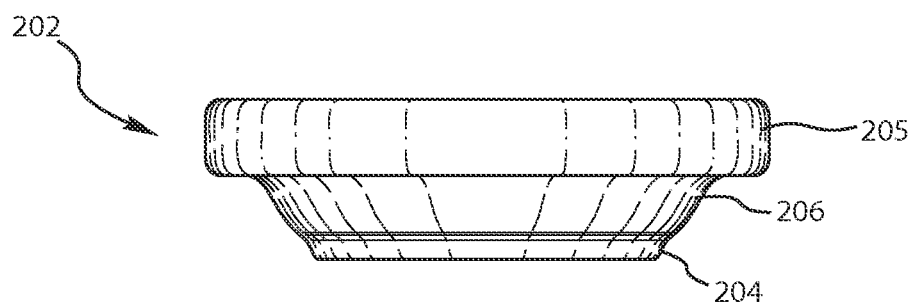
FIG. 7 is a side view of the ceramic scent bowl of FIG. 6.
Figure 8:
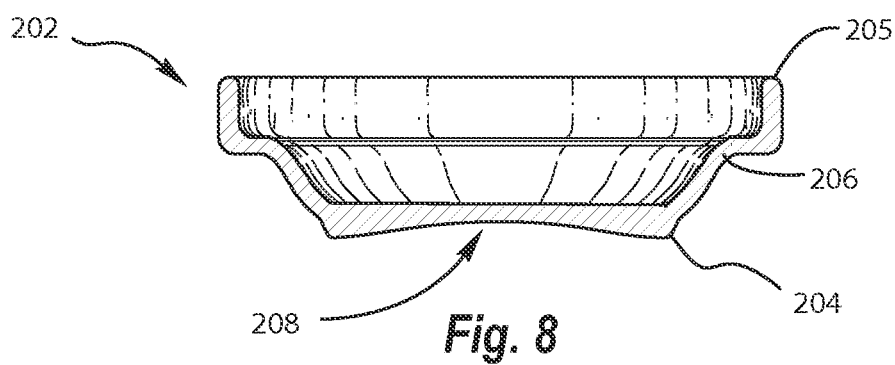
FIG. 8 is a cross sectional view of the ceramic scent bowl of FIG. 6 taken along line 8-8 of FIG. 6.

For the exemplary purposes of this disclosure and turning to FIGS. 6-8, scent bowl 202 is shown for use with a ceramic scent bowl warmer device 300. The bowl 202 is separate and detachable from warmer 300.

Scent bowl 202 includes a base 204 and at least one sidewall 206, wherein a majority of the base 204 and the at least one sidewall 206 is formed of ceramic material (and/or any inorganic clay materials such as porcelain or even alloys and metals that can maintain a similar temperature profile to ceramic materials or composites thereof) having a heat deflection temperature high enough to withstand the heat generated by the ceramic scent bowl warmer 300. It is believed that, different from the conventional glass and metal bowls, a ceramic or ceramic composite bowl will be more desirable from a safety and marketing standpoint, will provide better characteristics (fragrance throw, etc.), and that it will provide production advantages as well.

The sidewall 206 extending from base can taper outwardly to lip 205. Such an outwardly tapering sidewall 205 provides greater surface area to bowl 202, which helps in emitting fragrance as well. The bowl 202 may have a thickness of at least 1.5 to 2.5 millimeters, such as about 2 millimeters for example.

The base 204 of the bowl may comprise an external concave base surface. The external concave base surface may provide a pocket 208 where heated air generated from the heating surface 302 of scent bowl warmer 300 may be trapped. Such trapped, heated air may aid in the constant temperature achieved by the bowl 202 when in use on the scent warmer 300. The base 204 may also include an internal flat base surface 207 so that a scent emitter can be evenly dispersed across the surface and be able to be heated evenly. However, in another implementation, the internal surface of base 204 could be a recessed or concave surface to concentrate any scent emitter and minimize the thickness of the base 204 so that the internal surface can be heated to and reach a higher temperature if desired.

The bowl 202 may have an upper ledge or lip 205. A non-limiting example is illustrated in FIGS. 6-8 at a top edge of the bowl 202. Such a lip 205 allows a user to pick up the bowl 202 easier, especially when on the scent bowl warmer 300. Lip 205 also provides greater surface area to bowl 202, which helps in emitting fragrance as well.

In terms of scent emitters that can be used, scented oil may be provided for use with the bowl 202. Alternatively, scented wax may be provided inside the bowl 202. The use of wax inside bowl 202, a balance needs to be had between the temperature of the scent warmer surface 302, the melting point of the scented wax (if used), the thickness of the wax (if used), and the ceramic material used to form bowl 202. If the wax has too high a melting point or is too thick, the wax may not liquefy completely from the heat of the warmer plate surface 302 resulting in an ineffective fragrance disbursement.

The scented wax may include a fragrance and a temperature at which the scented wax liquefies and evaporates fragrance. As discussed in relation to earlier embodiments herein, the scent bowl warmer 300 may be configured generate heat at a temperature hot enough to completely liquefy the scented wax in one to three hours. It has been determined that for most social gatherings where a scent bowl 202 and scent bowl warmer surface 302 is used, it is most desirable if fragrance begins to evaporate within 3 hours, and more desirable that it evaporate within 2 hours. In particular implementations, it is desirable for fragrance to evaporate in less than 1 hour. For specific implementations where the scent emitter is scented wax, it is desirable if the fragrance evaporates from the liquefied wax within 3 hours, or more desirably in less than 2 hours. In particular implementations, it is desirable for the scented wax to completely liquefy and fragrance to evaporate in less than 1 hour.

If scented wax is employed, the scented wax may include a scented wax bottom surface in surface communication with the internal surface 207 of base 204 of bowl 202 and a scented wax upper surface. Scented wax may comprise any animal wax, vegetable wax, mineral wax, petroleum wax or synthetic wax in compound with a fragrance. A fragrance may comprise any perfume, essential oil, or other aromatic compound, whether derived from a plant source, animal source, other natural source, or any synthetic source. It will be understood that where liquid fragrance is compounded with wax, the liquid fragrance may remain in its liquid state and may reside in the interstitial spaces between individual wax crystals.

In one particular implementation, the scented wax is formed of the same wax scented candles are made of. One example of a company that manufactures and sells scented candles is Gold Canyon International, Inc. of Arizona, USA. Wax, depending upon its physical properties related to the type of wax used, has a temperature at which it melts. Scented wax is wax that includes fragrance mixed with the wax. When the wax melts from a solid to a liquid, the fragrance trapped in the previously solid wax now turned liquid begins to evaporate.

In a particular implementation of scented wax, the temperature at which scented wax liquefies and evaporates fragrance is between 140° and 170° Fahrenheit. In other implementations, the temperature at which scented wax liquefies and evaporates fragrance is above about 113° Fahrenheit.

In other implementations, the ceramic scent bowl may contain a scent emitter in other forms than liquid oil or wax. Other forms of scent emitters include any substrate capable of carrying a fragrance such as, without limitation, wood, paper, cloth, felt, beads, gel, plastic, ceramic, glass, liquid, or other compound or material suitable for carrying a fragrance. It will be understood that, in implementations involving a scent emitter, the scent emitter may first be formed and thereafter impregnated with a fragrance, or the substrate may be impregnated with fragrance simultaneously with its forming. Thus for example, in particular implementations, the substrate may be a plastic bead infused with fragrance during production. As the plastic bead heats, it softens and a portion of the fragrance is permitted to evaporate from the plastic bead. In other particular implementations, a gel bead may be used.

Figure 9:
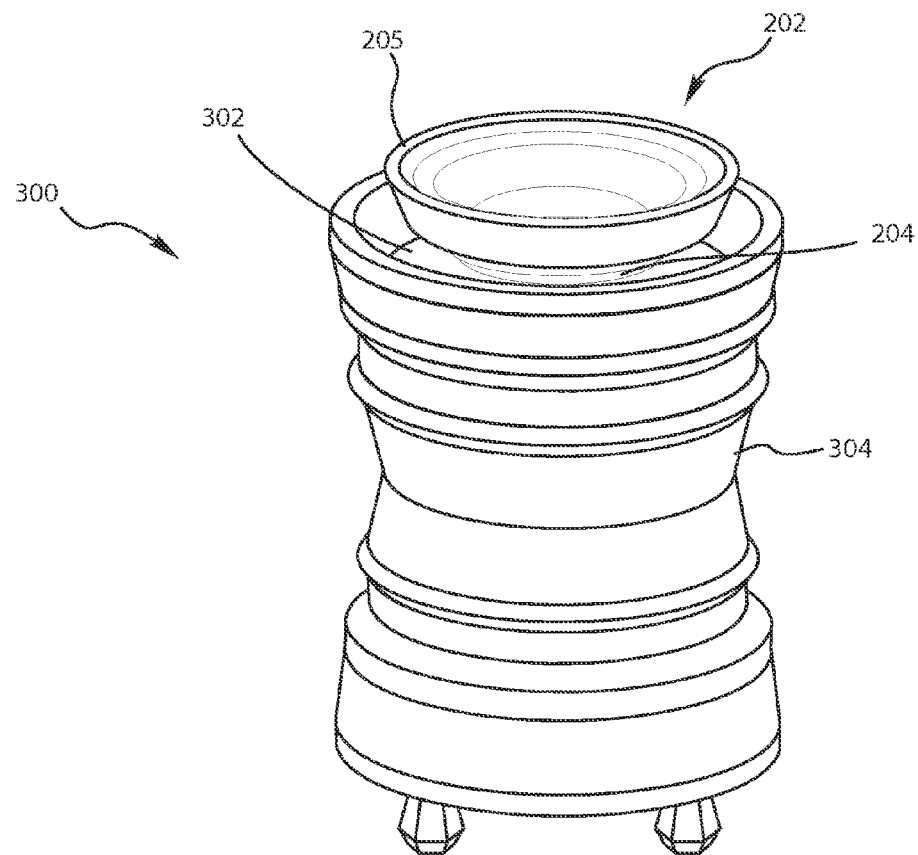
FIG. 9 is an in-use perspective view of a ceramic scent bowl warmer and the ceramic scent bowl of FIG. 6.
Figure 10:
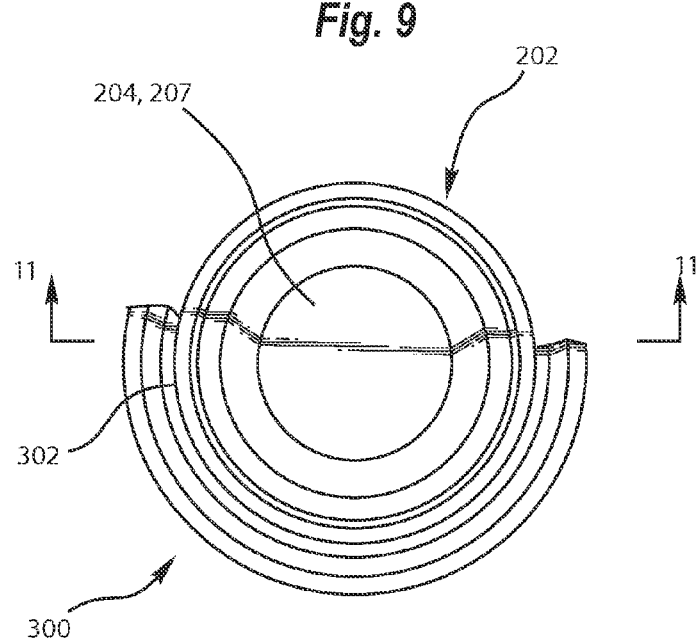
FIG. 10 is an top view of the in-use ceramic scent bowl warmer and the ceramic scent bowl of FIG. 9 with a portion of the scent bowl warmer broken away.
Figure 11:
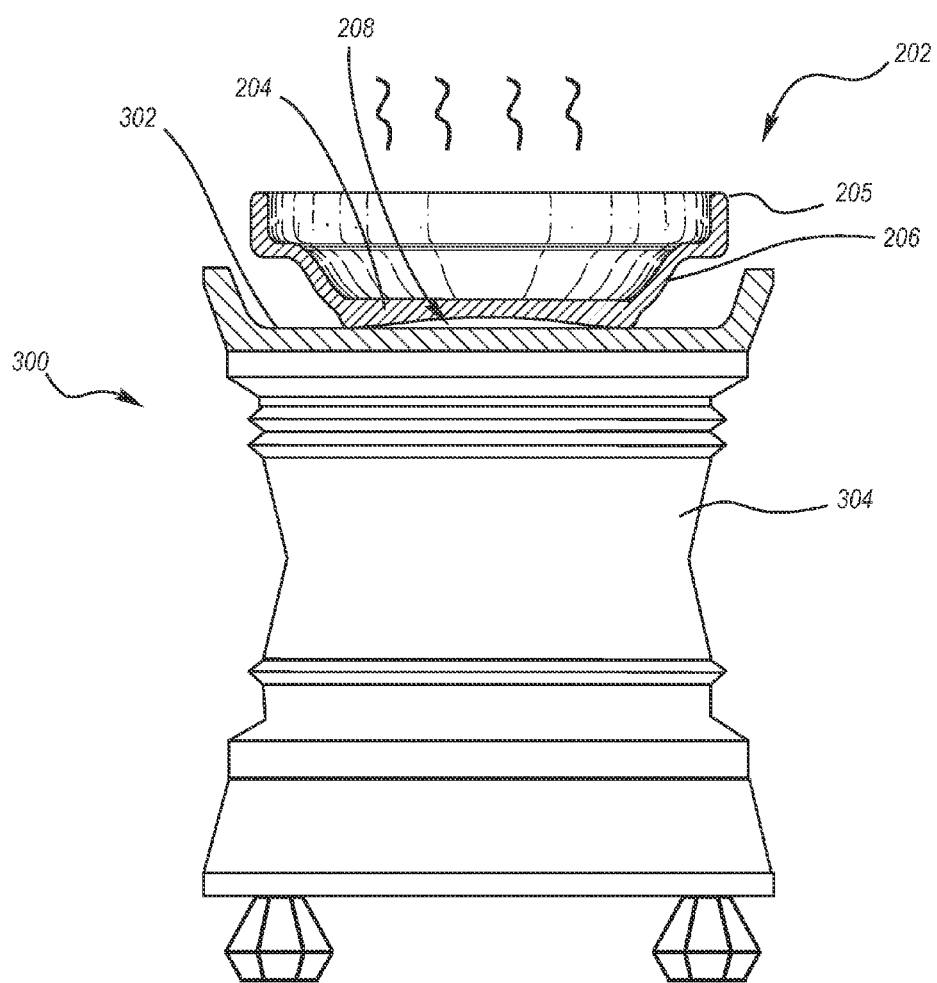
FIG. 11 is a partial cross sectional view of the in-use ceramic scent bowl warmer and the ceramic scent bowl of FIG. 9 taken along line 11-11 of FIG. 10.

For the exemplary purposes of this disclosure and turning to FIGS. 9-11, a system and method for scenting the air in a room is disclosed. Scent bowl 202 is shown in use with a scent bowl warmer 300. The bowl 202 is separate and detachable from warmer 300. Scent bowl warmer 300 is configured to generate heat at a first temperature. A scent emitter having a fragrance and a second temperature at which the fragrance evaporates may be provided in or placed in detachable and separate bowl 202. The first temperature generated by the scent warmer 300 can be high enough to evaporate at least a portion of the fragrance from the scent emitter in the bowl 202 in less than three hours. For example, the first temperature may be set so that it is no greater than 230° Fahrenheit. The second temperature may be approximately 175° Fahrenheit.

The ceramic scent bowl warmer surface 302 is heated with electricity or a flame in limited implementations, or other heating elements. In the particular implementation illustrated in FIGS. 3-5 and 9-11, the scent bowl warmer surface 302 comprises an electric resistor, which may be in electrical communication with a power outlet via power plug and electrical cord. Other heating elements are known in the art and are equally interchangeable with the non-limiting example provided here. Those of ordinary skill in the art can readily select appropriate materials for creating a warmer surface with a desired temperature. With power plug inserted in a power outlet, electricity flows through electrical cord to electrical resistor. Electrical resistor converts the electrical energy into heat energy. In particular implementations, scent bowl warmer surface 302 itself may comprise electrical resistor or other resistive or other heating element. In other implementations, electrical resistor may be coupled with scent bowl warmer surface 302 or adjacent to or separated from scent bowl warmer surface 302. In particular implementations, for safety, the temperature of scent bowl warmer surface 302 is designed so that it does not exceed 230° Fahrenheit.

In general and using scented wax as an example, a method for scenting the air in a room may include placing the external concave base surface of detachable and separate ceramic scent bowl 202 on the scent bowl warmer surface 302. If the ceramic scent bowl 202 did not already include either a fragrance oil or a scented wax and fragrance within the bowl 202, then an appropriate scent emitter can be added to bowl 202. Then the external concave base surface can be heated by the scent bowl warmer surface 302 by heating the warmer surface 302 to a temperature sufficient to completely liquefy the wax and evaporate at least a portion of the fragrance from the wax or oil. This may be done in less than three hours.

Specifically, a user may place scent bowl 202 on scent bowl warmer 302 so that base 204 of scent bowl 202 is in thermal communication with scent bowl warmer surface 302. As described above, the base 204 of the bowl 202 may comprise an external concave base surface. The external concave base surface provides a pocket 208 where heated air generated from the heating surface 302 of scent bowl warmer 300 may be trapped. Such trapped, heated air may aid in the constant temperature achieved by the bowl 202 when in use on the scent warmer 300. The base 204 may also include an internal flat base surface 207 so that a scent emitter can be evenly dispersed across the surface and able to be heated evenly. When the temperature of warmer surface 302 begins to increase (with base 204 of ceramic scent bowl 202 placed thereupon), the base 202 also begins to increase in temperature. Additionally, the thermal energy conducted from warmer surface 302 through base 204 continues to be conducted to the bottom surface of the scented wax, through scented wax, until it escapes through scented wax upper surface (which may carry fragrance with it). When heated from the bottom through the base 204, the scented wax liquefies beginning with the scented wax bottom surface, slowly through the scented wax until the scented wax upper surface liquefies. Generally, the scented wax upper surface begins liquefying at the center and moves outward to the edges until all of the scented wax upper surface, and all of the scented wax below it, is completely liquefied.

The surface area of the liquefied scented wax upper surface determines the amount of fragrance that evaporates from the scented wax. The greatest fragrance evaporation efficiency occurs when the scented wax upper surface has completely liquefied. For the scented wax used in the particular implementation described above, the scented wax liquefies most efficiently, and safely, at a temperature range of between 140° and 170° Fahrenheit. It was found through testing that with approximately ¾ inches thick of scented wax in a bowl 202 having a base thickness of around 1.8 millimeters and an opening diameter of about 3.75 inches, the scented wax could be completely liquefied in the bowl 202 in less than 3 hours. Temperatures closer to the bottom of the range yielded a longer melting time than temperatures closer to the top of the range. In other implementations, scented wax takes less than two hours to completely liquefy. In still other implementations, scented wax takes less than one hour to completely liquefy. It will be understood that the time in which scented wax completely liquefies may vary depending upon the temperature of scent bowl warmer surface 302, the thickness of base 204 of ceramic scent bowl 202, the thickness of scented wax within ceramic scent bowl 202, the melting point of scented wax, the ambient room temperature, and other factors.

Thus, in summary and by way of illustrating various advantages and benefits, ceramic scent bowl implementations are such that the temperature of the fragrance oil or scented wax can volatize at a certain rate (not too hot or too cold) and provide a good fragrance throw (intensity and strength). Ceramic bowls provide the right temperature (about 170° Fahrenheit), provide consistent fragrance release, and have a large surface area for better fragrance throw. All of these features provide better performance. For example, in 15 to 30 minutes with fragrance oils or in about an hour with scented wax, ceramic bowl implementations can provide candle strength (in character and intensity) fragrance throw.

Many additional implementations are possible. Further implementations are within the CLAIMS.

Specifications, Materials, Manufacture, Assembly

It will be understood that ceramic scent bowl and heating system implementations are not limited to the specific assemblies, devices and components disclosed in this document, as virtually any assemblies, devices and components consistent with the intended operation of a scent bowl and heating system implementation may be utilized. Accordingly, for example, although particular scent bowls, bases, surfaces, side walls, lips or ledges, heating elements, and other assemblies, devices and components are disclosed, such may comprise any shape, size, style, type, model, version, class, measurement, concentration, material, weight, quantity, and/or the like consistent with the intended operation of a scent bowl and heating system implementation. Implementations are not limited to uses of any specific assemblies, devices and components; provided that the assemblies, devices and components selected are consistent with the intended operation of a scent bowl and heating system implementation.

Implementations of ceramic scent bowls and implementing components may be constructed of a wide variety of materials. For example, the components may be formed of: ceramic, inorganic clay material and/or other like materials (e.g., porcelain, earthenware, silicon aluminium oxynitride, silicon carbide, magnesium silicate, and the like); metals, and/or other like materials; alloys and/or other like materials; composites of ceramic and metal (cermet) and/or other like materials; any other suitable material; and/or any combination of the foregoing thereof.

Some components defining a ceramic scent bowl and heating system implementations may be manufactured simultaneously and integrally joined with one another, while other components may be purchased pre-manufactured or manufactured separately and then assembled with the integral components. Various implementations may be manufactured using conventional procedures as added to and improved upon through the procedures described here.

Accordingly, manufacture of these components separately or simultaneously may involve injection molding, vacuum forming, blow molding, casting, forging, cold rolling, milling, drilling, reaming, turning, grinding, stamping, pressing, cutting, bending, welding, soldering, hardening, riveting, punching, plating, and/or the like. Components manufactured separately may then be coupled or removably coupled with the other integral components in any manner, such as with adhesive, a heat weld, a weld joint, a solder joint, a fastener (e.g. a bolt and a nut, a screw, a rivet, a pin, and/or the like), washers, retainers, wrapping, wiring, any combination thereof, and/or the like for example, depending on, among other considerations, the particular material forming the components.

In places where the description above refers to particular implementations of a ceramic scent bowl, it should be readily apparent that a number of modifications may be made without departing from the spirit thereof and that these implementations may be alternatively applied. The accompanying CLAIMS are intended to cover such modifications as would fall within the true spirit and scope of the disclosure set forth in this document. The presently disclosed implementations are, therefore, to be considered in all respects as illustrative and not restrictive, the scope of the disclosure being indicated by the appended CLAIMS rather than the foregoing DESCRIPTION. All changes that come within the meaning of and range of equivalency of the CLAIMS are intended to be embraced therein.

The invention claimed is:

1. A system for scenting the air in a room with scent from a scent bowl comprises:
    a scent bowl warmer configured to generate heat at a first temperature;
    a scent bowl detachable and separate from the scent bowl warmer, the scent bowl comprising:
        a base comprising an external concave base surface and at least one sidewall extending from the base, the external concave base surface defining a pocket in the base surface of the scent bowl where air heated by the scent bowl warmer is trapped and provides a consistent temperature to the scent bowl; and
        a scent emitter therein, the scent emitter having a fragrance and a fragrance evaporation point equal at which the fragrance evaporates;
    wherein the first temperature is high enough to evaporate at least a portion of the fragrance from the scent emitter in the bowl in less than three hours.

2. The system of claim 1, wherein the at least one sidewall tapers outwardly.

3. The system of claim 2, wherein a majority of the base and the at least one sidewall is formed of a ceramic material.

4. The system of claim 3, wherein the ceramic material comprises porcelain.

5. The system of claim 4, wherein the base of the bowl further comprises an internal flat base surface.

6. The system of claim 5, wherein the bowl has a thickness of about 1.5 to about 2.5 millimeters.

7. The system of claim 6, wherein the first temperature is set so that it is no greater than 230° Fahrenheit.

8. The system of claim 7, wherein the fragrance evaporation point is approximately 175° Fahrenheit.

9. The system of claim 8, wherein the scent emitter comprises one of scented oil and scented wax.

10. The system of claim 1, wherein an upper edge of the at least one sidewall comprises a lip that forms a top edge of the bowl, the lip configured to allow a user to pick up the bowl without touching the scent bowl warmer.

11. A scent bowl for use with a scent bowl warmer device comprising:
    a base sized to rest on a heating surface of the scent bowl warmer device and comprising an external concave base surface and an internal flat base surface, wherein the external concave base surface defines a pocket where air heated by the scent bowl warmer is trapped; and
    at least one sidewall extending from the base;
    wherein a majority of the base and the at least one sidewall is formed of a ceramic material.

12. The scent bowl of claim 11, wherein the at least one sidewall tapers outwardly.

13. The scent bowl of claim 11, wherein the ceramic material comprises porcelain.

14. The scent bowl of claim 13, wherein the bowl has a thickness of about 1.5 to about 2.5 millimeters.

15. The scent bowl of claim 1, wherein an upper edge of the at least one sidewall comprises a lip that forms a top edge of the bowl and is configured to allow a user to pick up the bowl.

16. A scent bowl for use with a scent bowl warmer device, comprising:
    a base sized to rest on a heating surface of the scent bowl warmer device and comprising an external base surface and an internal base surface, wherein the external base surface defines a pocket where air heated by the scent bowl warmer is trapped between the external base surface and the scent bowl warmer; and at least one sidewall extending from the base;

wherein a majority of the base and the at least one sidewall is formed of a ceramic material.

17. The scent bowl of claim 16, wherein the at least one sidewall tapers outwardly.

18. The scent bowl of claim 17, wherein the ceramic material comprises porcelain.

19. The scent bowl of claim 18, wherein the scent bowl base surface has a minimum thickness of about 1.5 to about 2.5 millimeters.

\* \* \* \* \*